United States Patent [19]

Givens et al.

[11] 4,052,472

[45] Oct. 4, 1977

[54] MORDENITE CONVERSION OF ALKANOLS TO PENTA- AND HEXAMETHYL BENZENES

[75] Inventors: Edwin Neil Givens, Pitman; Charles Joseph Plank, Woodbury; Edward Joseph Rosinski, Pedricktown, all of N.J.

[73] Assignee: Mobil Oil Corporation, New York, N.Y.

[21] Appl. No.: 649,771

[22] Filed: Jan. 16, 1976

[51] Int. Cl.² ............................................. C07C 1/20
[52] U.S. Cl. ........................... 260/668 B; 260/668 R; 260/668 A; 260/676 R; 260/682
[58] Field of Search ............ 260/668 R, 668 A, 668 B, 260/449 R, 682

[56] References Cited

U.S. PATENT DOCUMENTS

| 3,551,353 | 12/1970 | Chen et al. | 208/120 |
| 3,894,103 | 7/1975 | Chang et al. | 260/668 R |
| 3,911,041 | 10/1975 | Kaeding et al. | 260/668 R |
| 3,979,472 | 9/1976 | Bulter | 260/668 R |
| 3,998,898 | 12/1976 | Chang et al. | 260/668 R |

*Primary Examiner*—Veronica O'Keefe
*Attorney, Agent, or Firm*—Charles A. Huggett; Vincent J. Frilette

[57] ABSTRACT

By catalytic contact with the crystalline alumino-silicate zeolite, mordenite, having a silica to alumina ratio greater than about 15, methanol and/or methyl ethers are catalytically condensed to a mixture of hydrocarbons including polyalkylated aromatic hydrocarbons.

8 Claims, No Drawings

MORDENITE CONVERSION OF ALKANOLS TO PENTA- AND HEXAMETHYL BENZENES

BACKGROUND OF THE INVENTION

1. Field of the Invention

This invention is concerned with the manufacture of hydrocarbon mixtures from lower aliphatic alcohols and/or the simple or mixed ethers of such alcohols. In particular, it is concerned with conversion of methanol or methyl ethers by catalytic contact with a mordenite catalyst having a silica to alumina ratio greater than about 15.

2. Description of the Prior Art

There is increasing interest and need for new and efficient processes that convert non-petroleum raw materials to hydrocarbons useful as fuels, solvents, or petrochemicals. The present advanced state of snythetic fiber, plastics, rubber and fuels technology, which forms the basis for the economic and physical well-being of modern society, in large measure developed because of the abundance of low-cost petroleum. Recognition that petroleum is not a replenishable resource, and that its cost and availability are subject to drastic change, make it desirable to seek alternative ways for providing hydrocarbon fuels and chemical intermediates. The present invention, which utilizes, as raw material, alcohols that can be prepared from coal or from natural gas, or from petroleum by-products, or from agricultural products, is such a method since it can utilize non-petroleum raw materials exclusively.

The dehydration of alcohols, particularly ethanol to ethylene, by catalytic contact with hydrogen mordenite is disclosed in U.S. Pat. No. 3,244,766 issued Apr. 5, 1975.

A method of converting an organic polar compound by catalytic contact with a crystalline aluminosilicate catalyst, including mordenite, having a silica to alumina ratio more than 10 to 1 is disclosed in U.S. Pat. No. 3,728,408 issued Apr. 17, 1973.

A process of condensing aliphatic organic compounds, including alcohols, with a crystalline aluminosilicate zeolite catalyst having a silica to alumina ratio of at least about 12 and a constraint index of about 1 to 12 is disclosed in U.S. Pat. No. 3,894,107 issued July 8, 1975.

A proces of converting aliphatic ethers to a product comprising hydrocarbon compounds by catalytic contact with a crystalline aluminosilicate zeolite having a silica to alumina ratio of at least about 12 and a constraint index of about 1 to 12 is disclosed in U.S. Pat. No. 3,894,106 issued July 8, 1975.

A method for preparing dealuminized mordenite is disclosed in U.S. Pat. No. 3,551,353 issued Dec. 29, 1970.

SUMMARY OF THE INVENTION

It has now been found that a feed comprising methanol, dimethyl ether, methyl ethers of lower aliphatic alcohols, or mixtures thereof, are aggregatively converted, under conditions more fully described hereinafter, to hydrocarbons by contact with a mordenite catalyst having a silica to alumina ratio greater than 15, and preferably greater than about 25. The term aggregatively converted is used herein to signify that a substantial fraction of the hydrocarbon molecules that are formed contain more carbon atoms than are present in the individual alkyl groups of the aliphatic alcohol reactants, thus clearly distinguishing the process of this invention from conventional dehydration. Indeed, the process of the present invention can be used to convert methanol, for example, to hydrocarbon mixtures rich in pentamethyl and hexamethyl benzenes.

The above-recited silica to alumina ratio of the mordenite is a critical parameter of the catalyst used in the process of this invention, and is believed to be related to the protracted high conversion found with this catalyst. Whereas somehwat similar conversion processes are described in U.S. Pat. No. 3,894,107 and in U.S. Pat. No. 3,894,106, both of these processes require a catalyst having a "constraint index" of about 1 to 12. It is surprising to discover that the protracted high conversions of the process of the present invention are achieved with a mordenite catalyst having a contraint index of less than 1.

DESCRIPTION OF PREFERRED EMBODIMENTS

The catalyst used in the process of this invention comprises mordenite, a crystalline aluminosilicate zeolite having a particularly robust framework structure. The crystal structure, X-ray diffraction pattern and other properties of mordenite are described in pertinent portions (e.g. p. 231) of the book "Zeolite Molecular Sieves" by Donald W. Breck, published by John Wiley, New York, N.Y. (1974) which portions are incorporated herein by reference as background material.

Mordenite is found in nature as amigdules and as sedimentary deposits at various locations in the United States, Japan and elsewhere. The typical unit cell content of the mineral, natural mordenite, is given by the formula

$$M_{x/n}[(AlO_2)_x(SiO_2)_{40}] \cdot 24 H_2O$$

wherein M is an alkali or alkaline earth metal cation or mixture thereof, and n is the valence of the cation. Sodium, calcium and potassium are the commonly occurring cations. The composition of the rigid, three-dimensional framework of the zeolite, consisting of aluminum and silicon atoms tetrahedrally bonded through oxygen bridges, is shown contained within the square brackets of the formula. In natural deposits, the molar ratio of $SiO_2$ to $Al_2O_3$, hereinafter referred to simply as the silica to alumina ratio, usually varies from about 8 to about 10. It is to be understood, of course, that all references made herein to silica to alumina ratio refer to the composition of the rigid, three-dimensional framework structure of the zeolite, and are intended to exclude binder components, impurities and aluminum cations within the channels of the framework.

Although the catalyst itself and its preparation are not considered part of the present invention, it is important to recognize that all mordenites are not effective in the process of this invention. For example, the natural mordenites described above, with a silica to alumina ratio of about 10, are not suitable before some treatment to impart the required silica to alumina ratio greater than 15. Such treatment is known to those skilled in the art, and is referred to as "dealuminization". Whereas any method of dealuminization may be used, such as leaching with mineral acid, a preferred one is described in U.S. Pat. No. 3,551,353 issued Dec. 29, 1970, the entire contents of which are incorporated herein by reference. In this method, powdered natural mordenite is contacted with steam and a mineral acid in multiple alternate cycles of steaming and refluxing in acid until the desired silica to alumina ratio is achieved.

Techniques for preparing synthetic mordenites are described in the literature and such material is commercially available from the Norton Company of Worcester, Mass. under the designation "Zeolon". As synthesized, synthetic mordenite usually has a composition similar to that described above for natural mordenite, i.e. the silica to alumina ratio of such mordenite as prepared is about 10. These mordenites may be treated as described above to increase the silica to alumina content to a ratio greater than 15 and preferably greater than about 25. As will be illustrated hereinafter, synthetic mordenite may be prepared by a special technique to provide crystals that have a silica to alumina ratio greater than about 15 in the as-prepared state. These are useful in the process of this invention without further dealuminization, or they may be further dealuminized if desired.

Whereas the minimum silica to alumina ratio required to provide the protracted, high conversions of the process of this invention has been specified, there is no precise maximum for this value. Mordenites with a silica to alumina ratio of about 30 or 50 are eminently suitable, and those having values of about 100 are operable. However, in spite of the fact that too much aluminum is detrimental to protracted activity, as demonstrated by the process of this invention, the other extreme too is expected to cause an adverse effect on conversion, i.e. it would appear not only unnecessary but inadvisable to employ mordenites having a silica to alumina ratio in excess of about 200.

For the purpose of the present invention, it is preferred to use the hydrogen form of the mordenite having the prescribed silica to alumina ratio. This may be prepared by ion-exchanging natural or synthetic mordenite with mineral acid, which results in exchange of hydrogen for the metallic cations in the mordenite. Ion-exchange may be done prior to, concurrent with, or after dealuminization. Alternatively, a mordenite having the appropriate silica to alumina ratio may be base exchanged with ammonium cations and the resulting ammonium form calcined to convert it to the hydrogen form.

Cations of metals from Group I through Group VIII of the Periodic Table may be present in the mordenite catalyst. In general, not more than about 80% of the total cation sites should be occupied by metal cations, the balance being hydrogen or a hydrogen precursor such as ammonium. In particular, it should be noted that if the catalyst were completely exchanged with a strongly basic alkali metal cation, such as sodium, it would be essentially inactive in the present invention. Furthermore, certain cations, such as aluminum, when present in too high a concentration in the mordenite, may effectively hinder the sorption and conversion of reactant molecules. Thus, regardless of which metal cations are present, the metal cation content should in no case exceed that which will reduce the usual sorption capacity of the mordenite for cyclohexane, which is about 5 to 6 wt. %, to a value below abou 2 wt. %. The sorption capacity referred to herein is to be measured by contacting the anhydrous zeolite with cyclohexane at about 50 mm vapor pressure, at about 25° C, until equilibrium is established.

The mordenite catalysts useful in the present invention possess a "constraint index" of less than about 1. A simple determination of the constraint index may be made by passing continuously a mixture of equal weight of normal hexane and 3-methylpentane over a small sample, approximately 1 gram or less, of catalyst at atmospheric pressure according to the following procedure. A sample of the catalyst, in the form of pellets or extrudate is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° F and 950° F to give an overall conversion between 10% and 60%. The mixture of hydrocarbons is passed at 1 liquid hourly space velocity (i.e. 1 volume of hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons.

The catalyst for this invention may be in the form of pellets or extrudate of about 1/8 to 1/4 inches diameter, or in the form of powders for operating in the fluidized state and having a particle size of about 10 to 100 microns. They may contain binders such as clay, silica alumina, alumina, carbon or other suitable matrix material. In general, it is preferred that the catalyst particles contain at least about 20 wt.% of the mordenite zeolite material, most preferably at least 60 wt.% The catalysts used in this invention, regardless of silica to alumina ratio and regardless of the presence or absence of metal cations, will have an X-ray diffraction pattern of mordenite, i.e. the X-ray diffraction pattern will exhibit at least the principle lines of mordenite, albeit these may be very slightly displaced as a consequence of a small contraction in the unit cell dimensions commonly experienced with high silica to alumina zeolites when compared with the natrual zeolite.

Feeds contemplated as within the scope of this invention include methanol produced by the destructive distillation of wood; and crude or purified methanol produced as the principal product or as co-product with dimethyl ether in processes based on the catalyzed reduction of carbon monoxide with hydrogen. Notable among such processes is the well-established industrial synthesis of methanol. As presently practiced, this process produces high purity methanol. However, catalyst and/or process modifications are known which produce good yields of methanol together with dimethyl ether, or a mixture of methanol with other lower aliphatic alcohols and the corresponding methyl ethers. The preferred feed to the process of this invention comprises aliphatic oxygenated compounds selected from the group consisting of methanol, methyl ethers of lower aliphatic alcohols containing up to four carbon atoms, and mixtures thereof. The methyl ethers include dimethyl ether, methyl-ethyl ether, methyl-n-propyl ether, methyl-isopropyl ether methyl-n-butyl ether, methyl-sec-butyl ether, methyl-isobutyl ether, and methyl tert-butyl ether. The particularly preferred feed comprises compounds selected from the group consisting of methanol, dimethyl ether, and mixtures thereof.

Regardless of the source of the feed, it need not be highly purified for use in the present invention. It is an attribute of this invention that other oxygenated compounds such as ethanol and higher alcohols, esters, acetals, ketones and the like will often convert to hydrocarbons along with the alcohols. Basic nitrogen compounds, such as pyridine and quinoline, however, are an exception since they may tend to deactivate the catalyst. The feed should be substantially free of basic nitrogen compounds.

Because catalyst activity may vary depending on extent of dealuminization and the possible presence of moderating cations in the catalyst — and because the particular composition of the feed and the particular product distribution desired may vary depending on circumstances, the contacting of the feed with the mordenite catalyst may be at an elevated temperature up to 1000° F, preferably from about 500° F to about 850° F, at a weight hourly space velocity (i.e. pounds of feed per pound of catalyst per hour, abbreviated herein W.H.S.V.) of 0.1 to 30 W.H.S.V. It is preferred to employ a W.H.S.V. of about 0.5 to about 10. A suitable pressure for said contacting is 0.1 to 50 atmospheres. These pressures refer essentially to the partial pressure of the reactant when diluents are employed. Inert diluents such as steam, nitrogen gas, flue gas and methane may be used. Hydrogen also may be used as diluent. Substantially inert aliphatic hydrocarbons such as ethane and propane also may be used as diluents. When diluents are used, the total pressure, may be up to 150 atmospheres.

Ordinary hydrogen mordenite, with a silica to alumina ratio less than 15, induces ordinary dehydration as the predominant protracted catalytic activity under the process conditions of this invention. As illustrated by the examples which follow, the principal product with a methanol feed usually is dimethyl ether, and conversions tend to be low. Some aggregative condensation does take place, but no substantial, useful activity of this type on a protracted basis is in evidence.

In contrast, in the process of this invention, wherein dealuminized mordenite is used, less than about 10% of the hydrocarbons from a methanol feed is methane, the balance being aggregatively condensed hydrocarbons. More than 25%, and usually more than about 50%, of the hydrocarbons produced are in boiling range of $C_5+$, i.e. pentanes and higher. Furthermmore, a major fraction of the $C_5+$ products in the hydrocarbon mixture usually is composed of aromatic hydrocarbons. The aromatic hydrocarbons range in molecular weight from benzene and toluene through tetra, penta and hexamethyl benzenes. Thus, the process of this invention is characterized by a pronounced activity for aggregative condensation. The other distinguishing feature of this invention is that the conversion of feed is high and is sustained at high levels for useful periods of time, at least for more than one hour. As illustrated by the examples hereunder, 80% conversion of feed is achieved, and usually substantially complete conversion is obtained, i.e. 90% or more of the methanol or dimethyl ether is converted.

The hydrocarbon mixtures produced in the process of this invention may be separated from the water also produced, and used directly as fuel. Alternatively, the hydrocarbon mixture may be distilled to recover a gasoline boiling range fraction, a diesel or fuel oil fraction, and/or other fractions useful as fuels or petrochemicals.

The following Examples are illustrative of this invention without being limiting on the scope thereof. All parts and percentages are by weight unless otherwise specified.

EXAMPLE 1

Dealuminized mordenite was prepared as follows:

Four and one-half pounds of synthetic mordenite (Norton Company Zeolon 100, powder) was contacted with a 2 wt.% solution of HCl using 7.5 cc of solution per gram of mordenite. Zeolon 100 H has a composition reported to be as follows: 0.5% Na, 0.2% Fe, 0.35% Ti, 0.1% Ca, 0.1% Mg, 0.1% $SO_3$, and a $SiO_2/Al_2O_3$ ratio about 10. The mordenite was contacted with the acid solution under stirred conditions for 2 hours heating up to and holding at 146° F. After the contact the slurry was settled and the excess solution poured off. This acid treatment was repeated twice more for 3-4 hours at a maximum temperature of 165° F. The treated mordenite was then water washed free of chloride ion, dried at 340° F, calcined for 10 hours at 1000° F and then steamed for 16 hours at 1000° F with steam at atmospheric pressure. The steamed acid treated mordenite was retreated 3 times employing a 2 wt. % HCl solution for 3 hours at about 180° F using 7.5 cc HCl solution per gram of mordenite. Between each contact the slurry was settled and decanted. Finally the treated mordenite was filtered and water washed free of chloride ions. The washed treated mordenite was dried at 230° F, pelleted and sized 14 to 25 mesh followed by calcination at 1000° F for 10 hours. The product analyzed 47/1 $SiO_2/Al_2O_3$ ratio.

EXAMPLE 2 methyl alcohol was passed over 1.0 gram (about 2 cubic centimeters volume) of the catalyst of Example 1 at a rate of 3.7 ml per hour. The catalyst bed, contained in a tubular glass reactor, had a 2¼ inch axial length. The catalyst was pretreated in place with an air flow of 10 cc/min at 1000° F for 1.5 hours followed by a nitrogen purge of 10 cc/min for 10 minutes while the temperature dropped to 600° F. When the MeOH flow was started the nearly isothermal temperature condition across the bed changed dramatically. The temperature across the bed at 4.5 hours on stream is shown in Table 1. The effluent from the catalyst was collected between 3.5 and 4.5 hours on stream. The run conditions and product distributions are shown in Table 2. In this run 98.2wt.% of the MeOH was converted of which 42.0 wt.% went to HC product, the balance being water. The hydrocarbon phase contained 64.2 wt.% $C_5+$ product.

EXAMPLE 3

The conditions for this example were essentially the same as for Example 2 except the temperature to which the catalyst was cooled after the thermal air treat was 700° F. After 4.5 hours on stream, the temperature maxima across the bed was 752° F (Table 1). The product distribution shown in Table 2 shows essentially complete conversion of methanol with 44.3 wt.% of the methanol being converted to hydrocarbon product. This represents the maximum theoretical yield of hydrocarbon. The hydrocarbon phase contained 59.4 wt.% $C_5+$ material.

EXAMPLE 4

Dimethyl ether was passed over 1.0 gram of the catalyst of Example 1 at a rate of one liter per hour while using the same reactor employed in Examples 2 and 3. The pretreatment was the same as used in Example 3 except the catalyst was heated in a flow of air for only one hour rather than for 1.5 hours. Then the catalyst was cooled to 700° F in nitrogen. The temperature maximum across the bed after 5 hours on stream was 790° F (Table 1). The product distributions of effluent collected between 4 and 5 hours on stream are shown in Table 2. In this run the dimethyl ether was essentially all converted. The product contained 69.8 wt.% hydrocarbons of which 68 wt.% was C5+.

EXAMPLE 5

A sample of commercially available Zeolon H, Type 100 (from Norton Company) material was pelleted and sized to 14 to 25 mesh particles and calcined 10 hours at 1000° F. This catalyst had a $SiO_2/Al_2O_3$ ratio of only 11.1.

EXAMPLE 6

Methanol was passed over 1.0 gram of the catalyst of Example 5 at a rate of b 3.84 ml per hour. The reactor catalyst bed configuration and pretreatment technique were essentially the same as described in Example 2 except the air pretreatment at 1000° F was for only 1.25 hours instead of 1.5 hours. The bed temperature profile after 5 hours on stream is shown in Table 1. The total effluent from the catalyst bed was collected between 4 and 5 hours on stream. The run conditions and product distributions are shown in Table 2. Under these reaction conditions 73.6 wt.% methanol was converted. Only 4.5 wt.% of the converted MeOH, or 3.3 wt.% of the charged MeOH, went to hydrocarbon product. Most of the converted MeOH went to DME (dimethyl ether) plus water.

EXAMPLE 7

One gram of the catalyst of Example 5 was placed in a reactor and calcined with air at a flow of 10 cc/min at 1000° F for 2 hours. The temperature was dropped to 600° F, the system purged with a 10 cc/min flow of nitrogen for 10 minutes and DME passed over the catalyst at a rate of one l./hr. The effluent from the catalyst bed was collected from 1 to 2 hours on stream. The run conditions and product distribution are shown in Table 2. Only 16 wt.% of the charged DME was converted of which 58.0 wt.% was hydrocarbon product. Only 6.9 wt.% of the HC phase was C5+ material.

EXAMPLE 8

Acid treated natural mordenite was prepared by the following procedure.

Forty grams of natural mordenite purchased from Wards Natural Science Establishment was sized to 14 × 25 mesh and then contacted four times for three hours each, at 190° F, with a 5 wt.% HCl solution, using 10 ml HCl solution per gram of starting mordenite. The treated natural mordenite was then water washed free of chloride ion, dried at 230° F for 21 hours, and finally calcined for 10 hours at 1000° F.

Final product compositions and properties were as follows:

| Composition | Na, wt.% | 0.61 |  |
|---|---|---|---|
|  | K, " | 0.35 |  |
|  | $SiO_2$, " | 83.9 |  |
|  | $Al_2O_3$," | 12.8 |  |
|  | Molar Ratio $SiO_2/Al_2O_3$ = 11/1 |  |  |
| Properties | Surface Area, 366 m²/g |  |  |
|  | Sorption, wt.% cyclohexane |  | 6.4 |
|  | n-hexane |  | 5.4 |
|  | $H_2O$ |  | 13.0 |

The calcined sample showed the X-ray diffraction properties of mordenite.

Methanol was passed over 1.0 gram of the above catalyst at a rate of 3.71 ml per hour. The reactor was the same as used in Example 2 with the catalyst bed having an axial measurement of 1⅜ inches. The pretreat conditions were identical with those of Example 2. The temperature profile of the catalyst bed is shown in Table 1. The run conditions and product distributions for reactor effluent collected between 4 and 5 hours on stream are shown in Table 2. Only 24.4 wt.% of the charged MeOH was converted of which only 9.5 wt.% (or 2.3 wt.% of charged MeOH) went to hydrocarbon product.

EXAMPLE 9

Methanol was passed over 1.0 gram of the catalyst described in Example 8 under identical conditions except at a nominal temperature of 700° F. The temperature profile is shown in Table 1. Only 19.2 wt.% methanol was converted of which only 2.2 wt.% went to hydrocarbon product.

EXAMPLE 10

Methanol was passed over a synthetic high-silica mordenite prepared by the following method:

A. Sodium aluminate solution
 35.1 g $NaAlO_2$ (43.1 wt.% $Al_2O_3$; 33.1 wt.% $Na_2O$; 24.3 wt.% $H_2O$)
 74.4 g NaOH
 175 g Water
B. Organic Salt
 196.5 g. tetraethylammonium (TEA) bromide
C. Silicate solution
 910 g colloidal silica sol (30% $SiO_2$)

These materials were mixed together by adding C to solution A, mixing thoroughly, then adding B followed by 5 minutes mixing. The mixture was then charged to a 2 liter Parr autoclave and held at 175° C for 3 days pressures to 400 psig with stirring. The resulting product was separated from the liquid by filtering and washing. Its $SiO_2/Al_2O_3$ ratio was 30 to 1.

The crystalline product, identified as mordenite by x-ray analysis, was first heated in $N_2$ for 3 hours at 1000° F and then exchanged with $NH_4Cl$ to remove residual sodium. In the exchange process 61.9 grams of the Na (TEA) mordenite were contacted with 620 ml of 10% $NH_4Cl$ solution for two hours at approximately 180°-200° F. After repeating the $NH_4Cl$ exchange four times the TEA mordenite was washed until essentially free of chloride ions. The cake was dried at 230° F, pelleted and sized to 14 × 25 mesh and recalcined 10 hours at 1000° F.

A 1.0 g portion of the above catalyst was tested in a manner essentially the same as the method described in Example 2 except the temperature to which the catalyst was cooled after the thermal air treat was 700° F.

After 2 hours on stream the temperature maxima in the bed was 721° F (Table 1). The product distribution in Table 2 shows 92.3 wt.% of the methanol was converted with 40% of the converted methanol going to hydrocarbon product.

It is evident from the foregoing examples that the process of the present invention has a sustained capability for aggregatively condensing aliphatic oxygenated organic compounds to hydrocarbons. That methanol and dimethyl ether are so converted, with the formation of a hydrocarbon mixture containing less than 10 weight percent methane, is evident from Table 2. Also, the heavy aromatics, such as the C-11 fraction, usually contain a major fraction of methyl benzenes (e.g. pentamethyl benzene). Furthermore, the conversion, unlike ordinary dehydration, is markedly exothermic. In large scale operation, therefore, it may be expedient to conduct the conversion in more than one stage with multiple reactors and with interstage cooling; or in a single reactor provided with recycle and/or internal cooling means such as liquid propane injection. In any case, such variants are familiar to those skilled in the art of conducting exothermic reactions. Such variants therefore are within the scope of this invention and may be practiced without departing rom the spirit thereof.

TABLE 1

CATALYST BED TEMPERATURE PROFILES AT NOTED TIME ON STREAM

| Example No. | 2 | 3 | 4 | 6 | 8 | 9 | 10 |
|---|---|---|---|---|---|---|---|
| Axial Bed Length (total inches) | 2¼ | 2¼ | 2¼ | 2¼ | 1⅛ | 1⅛ | 2¼ |
| Temp ° F, inches from top | | | | | | | |
| 0 | NA | NA | 790 | NA | NA | NA | NA |
| ½ | 570 | 752 | 732 | 611 | 608 | 701 | 721 |
| 1 | 664 | 706 | 665 | 606 | 607 | 698 | 713 |
| 1½ | 685 | 704 | 680 | 600 | 613¹ | 709¹ | 709 |
| 2 | 596 | 714 | 683 | 608 | — | — | 713 |
| 2⅛ | — | — | — | — | — | — | 700 |

TABLE 1-continued

CATALYST BED TEMPERATURE PROFILES AT NOTED TIME ON STREAM

| Example No. | 2 | 3 | 4 | 6 | 8 | 9 | 10 |
|---|---|---|---|---|---|---|---|
| Hours on Stream | 4.5 | 4.5 | 5 | 5 | 5 | 5 | 2 |

¹Temp at 1⅛ inches
NA = not available

TABLE 2

| | Ex.2 | Ex.3 | Ex.4 | Ex.6 | Ex.7 | Ex.8 | Ex.9 | Ex.10 |
|---|---|---|---|---|---|---|---|---|
| $SiO_2/Al_2O_3$ | 47/1 | 47/1 | 47/1 | 11/1 | 11/1 | 11/1 | 11/1 | 30/1 |
| Feed | MeOH | MeOH | DME | MeOH | DME | MeOH | MeOH | MeOH |
| WHSV of Feed | 2.9 | 2.9 | 1.9 | 3.0 | 1.9 | 2.9 | 3.0 | 2.9 |
| Temp. ° F, Average | 600 | 700 | 700 | 600 | 600 | 607 | 700 | 700 |
| Maxima | 685 | 752 | 790 | 611 | ? | 613 | 709 | 721 |
| Converted Feed, wt% | 98.2 | 99.6 | 99.4 | 73.6 | 16 | 24.4 | 19.2 | 92.3 |
| Products Based on Recovered Material | | | | | | | | |
| Methanol | — | — | 0 | — | 8.2 | — | — | — |
| DME | 0.4 | <0.1 | — | 57.7 | — | 57.7 | 63.9 | 16.3 |
| Water | 57.5 | 55.4 | 29.5 | 36.6 | 33.7 | 32.7 | 33.7 | 43.5 |
| Hydrocarbons | 42.0 | 44.3 | 69.8 | 4.5 | 58.0 | 9.5 | 2.2 | 40.0 |
| Analysis HC Phase | | | | | | | | |
| C5 + wt.% | 64.2 | 59.4 | 68.0 | 24.0 | 6.9 | 79.0 | (1) | 53.5 |
| Methane | 0.8 | 1.6 | 1.1 | 4.6 | 17.9 | 2.0 | | 5.1 |
| Ethylene | 3.9 | 4.5 | 3.4 | 16.8 | 22.1 | 3.4 | | 10.7 |
| Ethane | 0 | 0.2 | 0.1 | 0 | 1.2 | 0.4 | | 0.3 |
| Propylene | 2.3 | 11.0 | 4.7 | 12.0 | 15.6 | 5.1 | | 6.4 |
| Propane | 2.5 | 4.3 | 4.1 | 0 | 11.5 | 1.3 | | 14.1 |
| i-butane | 24.9 | 13.9 | 15.0 | 24.8 | 19.7 | 6.1 | | 3.1 |
| Butenes | 1.0 | 4.1 | 2.2 | 14.4 | 4.8 | 2.5 | | 2.4 |
| n-butane | 1.3 | 1.0 | 1.4 | 3.3 | 0 | 0 | | 4.4 |
| C5 + Product Analysis | | | | | | | | |
| Paraffins, Olefins, Benzene & Toluene, wt% | 44.8 | 38.3 | 20.7 | (1) | (1) | (1) | (1) | 36.7 |
| C8 Aromatics | 1.4 | 2.6 | 1.3 | | | | | — |
| C9 Aromatics | 2.3 | 3.8 | 1.3 | | | | | — |
| C10 & Heavier Arom. | 48.5 | 55.3 | 76.7 | | | | | 63.3 |
| Coke on Cat. wt% | 8.1 | 7.3 | 7.3 | 10.8 | 9.7 | 5.5 | 5.9 | 7.5 |

(1) Values too small for presentation.

What is claimed is:

1. A method for converting aliphatic oxygenated organic compounds to hydrocarbon mixtures, which comprises: contacting a feed comprising one or more oxygenated organic compounds selected from the group consisting of methanol and methyl ethers of the lower alkanols with a mordenite catalyst having a silica to alumina ratio greater than 15 and a constraint index of less than about 1, said contacting being at a temperature from about 500° F to about 850° F, a pressure of 0.1 atmosphere to 50 atmospheres, and a W.H.S.V. of 0.1 to 30; and converting at least about 80% of said oxygenated organic compounds to water and a hydrocarbon mixture containing less than 10 weight percent methane and more than about 50% of $C_9$, $C_{10}$ and heavier aromatics.

2. The method described in claim 1 wherein said contacting of said feed is at a W.H.S.V. of about 0.5 to about 10.

3. The method described in claim 1 including the step of calcining said mordenite catalyst in air at a temperature of about 850° F to about 1300° F prior to said contacting step.

4. The method described in claim 1 wherein said mordenite catalyst is in the hydrogen form.

5. The method described in claim 1 wherein said mordenite catalyst has a silica to alumina ratio greater than about 25 and has a sorption capacity for cyclohexane of at least about 2 wt. percent.

6. The method described in claim 5 wherein said mordenite catalyst is in the hydrogen form.

7. The method described in claim 6 wherein said feed consists essentially of methanol, dimethyl ether or mixtures thereof.

8. The method described in claim 6 including the step of calcining in air said mordenite catalyst having a silica to alumina ratio greater than about 25.

* * * * *